United States Patent
Ju et al.

(10) Patent No.: US 10,006,884 B1
(45) Date of Patent: Jun. 26, 2018

(54) METHOD AND APPARATUS FOR DETERMINING CURIE TEMPERATURE DISTRIBUTION OF A SAMPLE OF MAGNETIC MATERIAL

(71) Applicant: Seagate Technology LLC, Cupertino, CA (US)

(72) Inventors: Ganping Ju, Pleasanton, CA (US); Jason L Presseky, Menlo Park, CA (US); Roy W. Chantrell, Anglesey (GB); Xiaowei Wu, Pleasanton, CA (US); Xi Chen, Fremont, CA (US); Xiaobin Zhu, San Ramon, CA (US); Yingguo Peng, San Ramon, CA (US)

(73) Assignee: Seagate Technology LLC, Cupertino, CA (US)

( * ) Notice: Subject to any disclaimer, the term of this patent is extended or adjusted under 35 U.S.C. 154(b) by 204 days.

(21) Appl. No.: 14/822,103

(22) Filed: Aug. 10, 2015

Related U.S. Application Data

(62) Division of application No. 13/249,893, filed on Sep. 30, 2011, now Pat. No. 9,103,729.

(51) Int. Cl.
  *G01R 33/00* (2006.01)
  *G01N 27/80* (2006.01)
(52) U.S. Cl.
  CPC ................................ *G01N 27/80* (2013.01)
(58) Field of Classification Search
  CPC ..................................................... G01R 33/00
  USPC ........................................................ 324/203
  See application file for complete search history.

(56) References Cited

U.S. PATENT DOCUMENTS

| | | | |
|---|---|---|---|
| 3,736,500 A * | 5/1973 | Berkowitz et al. | ........... 324/203 |
| 5,448,067 A | 9/1995 | Micheli | |
| 5,563,852 A | 10/1996 | Murakami et al. | |
| 5,887,449 A | 3/1999 | Pecharsky et al. | |
| 6,483,299 B1 | 11/2002 | Presseky et al. | |
| 6,753,043 B1 | 6/2004 | Kuo et al. | |
| 6,855,439 B1 | 2/2005 | Rou et al. | |
| 7,166,997 B2 | 1/2007 | Ju et al. | |
| 8,787,124 B1 | 7/2014 | Chemyshov et al. | |
| 2004/0037202 A1 | 2/2004 | Brommer et al. | |

(Continued)

FOREIGN PATENT DOCUMENTS

| | | |
|---|---|---|
| EP | 1646057 | 4/2006 |
| ES | 2176194 T3 | 12/2002 |

OTHER PUBLICATIONS

Youssif et al., "AC Magnetic Susceptibility Technique for the Characterization of High Temperature Superconductors", Egypt. J. Sol., vol. 23, No. 2, 2000, pp. 231-250.

(Continued)

*Primary Examiner* — Bot Ledynh
(74) *Attorney, Agent, or Firm* — Hollingsworth Davis, LLC

(57) ABSTRACT

Determining a Curie temperature (Tc) distribution of a sample comprising magnetic material involves subjecting the sample to an electromagnetic field, heating the sample over a range of temperatures, generating a signal representative of a parameter of the sample that changes as a function of changing sample temperature while the sample is subjected to the electromagnetic field, and determining the Tc distribution of the sample using the generated signal and a multiplicity of predetermined parameters of the sample.

20 Claims, 13 Drawing Sheets

(56) References Cited

U.S. PATENT DOCUMENTS

| | | |
|---|---|---|
| 2004/0066190 A1 | 4/2004 | Ju et al. |
| 2009/0235500 A1 | 9/2009 | Jundt et al. |
| 2011/0058458 A1 | 3/2011 | Rasing et al. |
| 2011/0140688 A1* | 6/2011 | Yang .............................. 324/201 |
| 2012/0232831 A1 | 9/2012 | Mizuno et al. |
| 2014/0043707 A1 | 2/2014 | Tomikawa et al. |

OTHER PUBLICATIONS

File History of U.S. Appl. No. 13/249,893.

* cited by examiner

US 10,006,884 B1

METHOD AND APPARATUS FOR DETERMINING CURIE TEMPERATURE DISTRIBUTION OF A SAMPLE OF MAGNETIC MATERIAL

RELATED PATENT DOCUMENTS

This application is a divisional of U.S. patent application Ser. No. 13/249,893, filed Sep. 30, 2011, to which priority is claimed pursuant to 35 U.S.C. § 119(e), which is hereby incorporated herein by reference in its entirety.

BACKGROUND

The demand for increased areal densities in memory devices is typically addressed by decreasing the size of magnetic storage elements. Decreasing the size of the magnetic storage elements can result in a decrease in thermal stability of the storage elements. To store data reliably for very small bit sizes of a magnetic recording medium, for example, the magnetic medium is typically made of a material with a very high coercivity. At some capacity point, the bit size is so small and the coercivity is so high that the magnetic field needed for writing data cannot be made strong enough to permanently affect the data, and data can no longer be written to the recording medium.

Heat Assisted Magnetic Recording (HAMR) is a promising approach for breaking the areal density limit by temporarily and locally changing the coercivity of the magnetic storage medium by raising the temperature above the Curie temperature. At temperatures above the Curie temperature, the magnetic recording medium effectively loses coercivity and a realistically achievable magnetic write field, often referred to as the switching field, can be generated to write data to the recording medium.

SUMMARY

Embodiments of the disclosure are directed to determining a Curie temperature (Tc) distribution of magnetic material. Embodiments of the disclosure are directed to quantifying a Tc distribution of magnetic material heated to at least the Curie temperature of the magnetic material in the presence of an electromagnetic field. Embodiments are directed to methods and apparatuses for determining Tc distribution of a sample comprising magnetic material, such as all or a portion of a magnetic recording element or medium.

According to various embodiments, methods for determining a Tc distribution of a sample comprising magnetic material involve acquiring temperature dependent AC susceptibility data for the sample and determining the Tc distribution of the sample based on the acquired data and a multiplicity of predetermined parameters of the sample. According to some embodiments, methods for determining a Tc distribution of a sample comprising magnetic material involves subjecting the sample to an electromagnetic field, heating the sample over a range of temperatures, generating a signal representative of a parameter of the sample that changes as a function of changing sample temperature while the sample is subjected to the electromagnetic field, and determining the Tc distribution of the sample using the generated signal and a multiplicity of predetermined parameters of the sample.

In accordance with other embodiments, apparatuses for determining a Tc distribution of a sample comprising magnetic material includes a tester configured to produce temperature dependent AC susceptibility data for the sample, and a processor configured to determine the Tc distribution of the sample based on the tester data and a multiplicity of predetermined parameters of the sample. According to some embodiments, apparatuses for determining a Tc distribution of a sample comprising magnetic material includes an electromagnetic field generator and a heating unit operable for heating the sample over a range of temperatures. A tester is configured to generate a signal representative of a parameter of the sample that changes as a function of changing sample temperature while the sample is subjected to an electromagnetic field produced by the electromagnetic field generator. A processor includes an input for receiving the signal generated by the tester. The processor is configured to determine the Tc distribution of the sample using the generated signal and a multiplicity of predetermined parameters of the sample.

These and other features and aspects which characterize various embodiments can be understood in view of the following detailed discussion and the accompanying drawings.

DETAILED DESCRIPTION

Determining the Curie temperature distribution for a magnetic recording medium can be useful for enhancing media recording performance. Knowing the Curie temperature distribution for a magnetic recording medium can provide a number of manufacturing and performance enhancements. Knowing Tc allows media designers and manufactures to reduce the standard deviation of Tc distribution, which provides the opportunity to reduce media recording jitter and enables high linear density HAMR recording. Knowing Tc and its distribution provides the capability to correlate key parameters of magnetic media properties based on Tc distribution with recording performance. Knowing Tc distribution for magnetic recording media provides a key metric that enables designers and manufacturers to enhance the materials, structures, and fabrication methodologies used to manufacture high linear density HAMR media. However, practical and repeatable techniques for characterizing this important magnetic property of magnetic recording media have heretofore not been available. One particular difficulty lies in separating Tc distributions from other distributions, as well as performing high temperature measurements with good sensitivity and accuracy.

According to various embodiments, an apparatus for determining a Curie temperature distribution of a sample comprising magnetic material includes a tester configured to produce temperature dependent AC susceptibility data for the sample. A processor is configured to determine a Tc distribution of the sample based on the tester data and a number of predetermined parameters of the sample. According to other embodiments, a method for determining a Curie temperature distribution of a sample comprising magnetic material involves acquiring temperature dependent AC susceptibility data for the sample, and determining a Tc distribution of the sample based on the acquired data and a number of predetermined parameters of the sample. These and other aspects of various embodiments of the disclosure will now be described with reference to the attached figures.

Figure 1A:
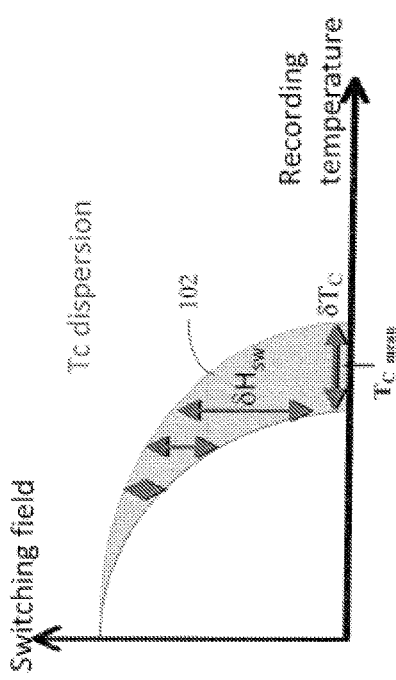
FIG. 1A graphically shows Curie temperature dispersion for a magnetic recording medium as a function of recording medium temperature, but with no anisotropy field ($H_k$) distribution, in accordance with various embodiments.
Figure 1B:
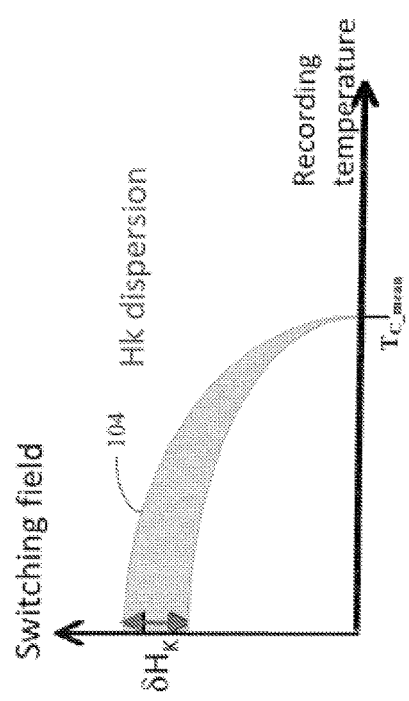
FIG. 1B graphically shows anisotropy field ($H_k$) dispersion for a magnetic recording medium as a function of recording medium temperature, but with no Tc distribution, in accordance with various embodiments.

FIG. 1A graphically shows Curie temperature dispersion 102 for a magnetic recording medium as a function of recording medium temperature, but with no anisotropy field ($H_k$) distribution. FIG. 1B graphically shows anisotropy field dispersion 104 for a magnetic recording medium as a function of recording medium temperature, but with no Tc distribution. As the recording medium temperature increases, the required switching field decreases and becomes easily achievable when the temperature of the recording medium reaches Tc. With a large number of grains distributed on a typical magnetic recording medium, there exists a Tc distribution as well as an anisotropy field ($H_k$) distribution of the medium. FIGS. 1A and 1B illustrate two extreme scenarios. While both Tc and $H_k$ distributions exist across a medium in reality, FIGS. 1A and 1B are intended to show that at a temperature around a Curie temperature mean of a recording medium, the switching field depends much more on the Tc dispersion than the $H_k$ dispersion.

Figure 2:
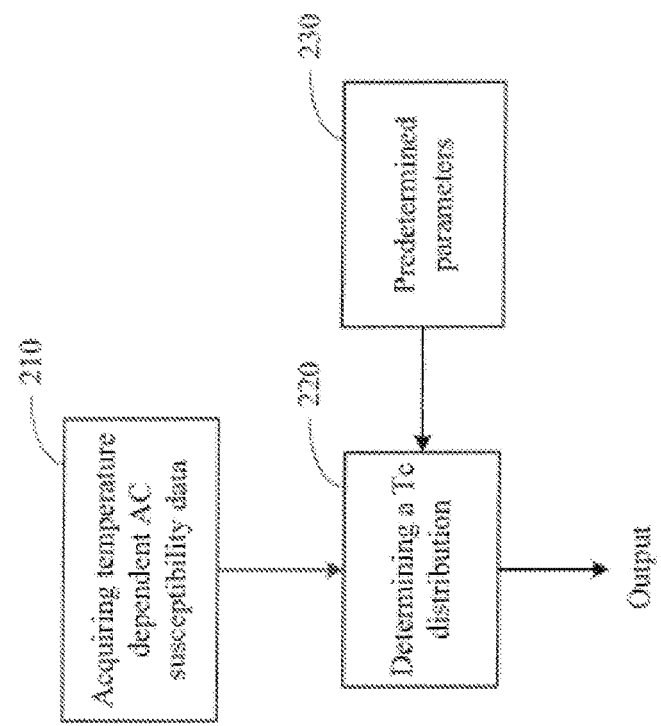
FIG. 2 illustrated various processes for determining Tc distribution for a sample comprising magnetic material in accordance with various embodiments.

Referring to FIG. 2, there is illustrated various processes for determining Tc distribution for a sample comprising magnetic material in accordance with various embodiments. The method illustrated in FIG. 2 involves acquiring 210 temperature dependent AC susceptibility data for the magnetic material sample. Using the AC susceptibility data and a number of predetermined parameters 230 associated with the magnetic material of the sample, a Tc distribution for the magnetic material sample is determined 220. An output is produced representative of the Tc distribution determination. Various forms of output can be reproduced, such as a signal, data, textual, audible, visual, and/or graphical information, for example.

Figure 3:
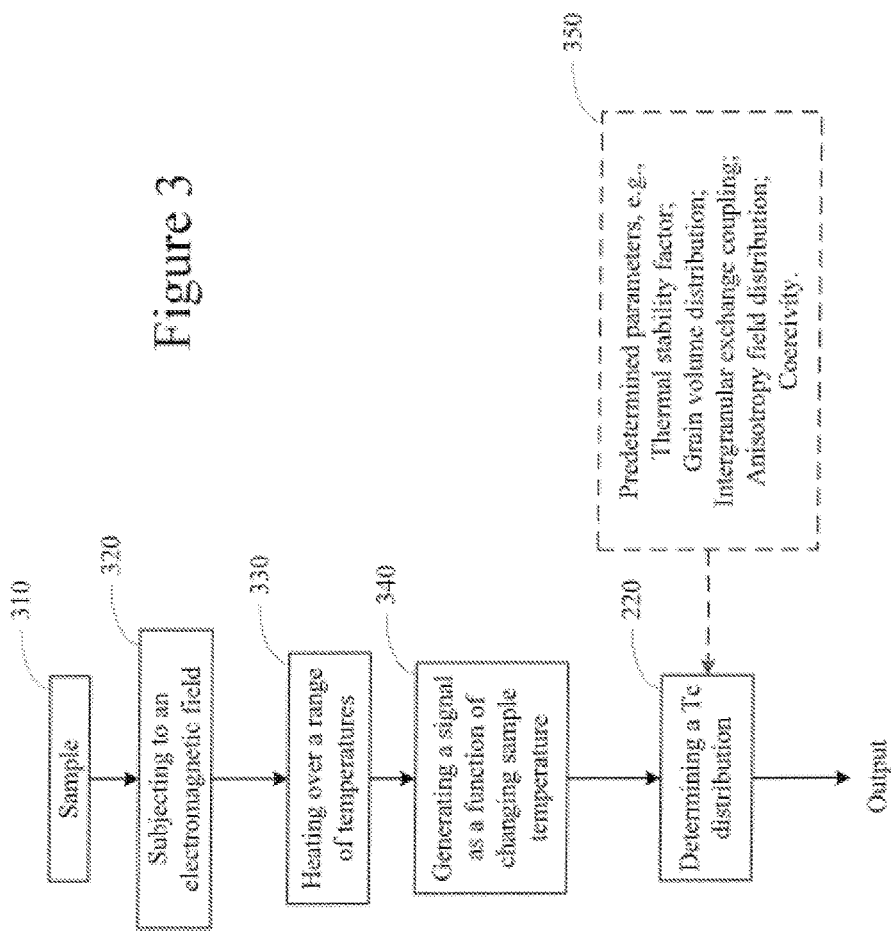
FIG. 3 shows various processes for determining Tc distribution for a sample comprising magnetic material in accordance with other embodiments.

FIG. 3 shows various processes for determining Tc distribution for a sample comprising magnetic material in accordance with other embodiments. According to the embodiment shown in FIG. 3, a sample 310 comprising magnetic material is subjected to testing. In particular, the sample 310 is subjected 320 to an electromagnetic field while being heated 330 over a predefined range of temperatures. The temperature range preferably includes a range of temperatures below and above a known Curie temperature (e.g., mean(Tc)) of the magnetic material sample. For example, a mean (or average) Curie temperature is known or can be estimated with a specified accuracy for a given magnetic material. The representative methodology shown in FIG. 3 involves raising the temperature of the sample 310 from a temperature below the mean Curie temperature for the sample, such as ambient or room temperature, to a temperature above the mean Curie temperature for the sample. The process further involves generating a signal 340 which changes as a function of changing sample temperature. Using the signal 340 and a number of predetermined parameters 350 obtained for the magnetic material sample, a distribution of Tc for the magnetic material sample is determined 220.

According to various embodiments, the predetermined parameters 350 shown in FIG. 3 include at least a minimum number of parameters required to compute Tc distribution for the sample 310. These predetermined parameters 350 are preferably measured using various known techniques. The number of predetermined parameters 350 constituting a "minimum number of parameters" is typically dependent on the specified degree of accuracy. In general, the accuracy of a Tc distribution determination increases as the number of predetermined parameters 350 used in the determination increases. By way of example, the minimum number of predetermined parameters 350 according to various embodiments corresponds to the number of parameters that strongly influence Tc distribution of the magnetic material sample, and excludes those parameters that weakly influence Tc distribution of the magnetic material sample.

In some representative embodiments, Tc distribution can be determined 220 using the following minimum number of predetermined parameters:

thermal stability factor ($K_U V/k_B T$), and
grain volume distribution ($\delta(V)$).

In other representative embodiments, Tc distribution can be determined 220 using the following minimum number of predetermined parameters:

thermal stability factor ($K_U V/k_B T$),
grain volume distribution ($\delta(V)$), and
intergranular exchange coupling (Hex).

where Ku is the energy density, V is the grain volume, $k_B$ is Boltzman's constant, and T is the absolute temperature. The following additional predetermined parameters weakly influence Tc distribution, but can be included to provide enhanced accuracy. These additional parameters include anisotropy field distribution ($\delta(H_k)$) and saturation magnetization (Ms). Those skilled in the art understand that a variety of known techniques can be used for measuring each of the predetermined parameters described herein.

In accordance with various embodiments, subjecting the sample 310 to an electromagnetic field 320 involves measuring temperature dependent AC susceptibility $\chi(T)$ using MOKE (Magneto-Optical Kerr Effect) detection. The measured temperature dependent AC susceptibility $\chi(T)$ is combined with other measured quantities (e.g., the predetermined parameters that strongly influence Tc distribution with or without the predetermined parameters that weakly influence the Tc distribution) to extract Tc distribution, thus enabling the quantification of this important magnetic media quantity. As is described in commonly owned U.S. Pat. No. 7,166,997, which is incorporated herein by reference, the temperature dependent AC susceptibility $\chi(T)$ originates from thermally activated switching. It is noted that AC susceptibility, also referred to as transverse AC susceptibility in the context of various embodiments, may be defined as the ratio of the AC field induced perpendicular magnetization and the AC field strength.

In a granular magnetic recording media, data is represented by the magnetic orientation of a bit. In each bit there is a multiplicity of grains which can be magnetically orientated in one of two ways along the easy axis of each grain. The magnetic orientation of the grains defines the state of the bit. When data is written to a bit, the orientation of that bit is switched. In order to switch the bit, the energy barrier of the magnetic material must be overcome. Normally, this is achieved by the writer of a disk drive system during write operations when the writer applies an external energy source to the bit.

According to U.S. Pat. No. 7,166,997, the energy barrier for a grain is reduced by applying an in-plain DC field to the grain. According to various embodiments of the present disclosure, the energy barrier for a grain is reduced by changing the temperature of the grain in relation to the Curie temperature of the grain. The energy barrier is thus a funcion of temperature in the context of embodiments of the disclosure, and depends on Tc and is distribution, as is characterized in the following equation:

$$\chi_i(T) = -\int_0^\infty f(Tc)dTc \frac{Ms(T/Tc)}{Hk(T/Tc)} \frac{1}{\langle V \rangle} \int VF(V)dV \int \frac{G(h_k)}{h_k} \frac{4W\beta\omega}{4W^2+\omega^2} dh_k$$

where $W=f_0 e^{-\beta}$ is the thermally activated transition rate; $f_0$ is the thermal attempt frequency; $\beta=K_U V/k_B T=M_S(T/Tc)*H_k(T/Tc)/2k_B T$; and $H_k(T/Tc)$ are functions of Ms and $H_k$ changing with temperature; and f(Tc), F(V), and $G(h_k)$ are distribution functional for Tc, grain volume and $H_k$.

Figure 4:
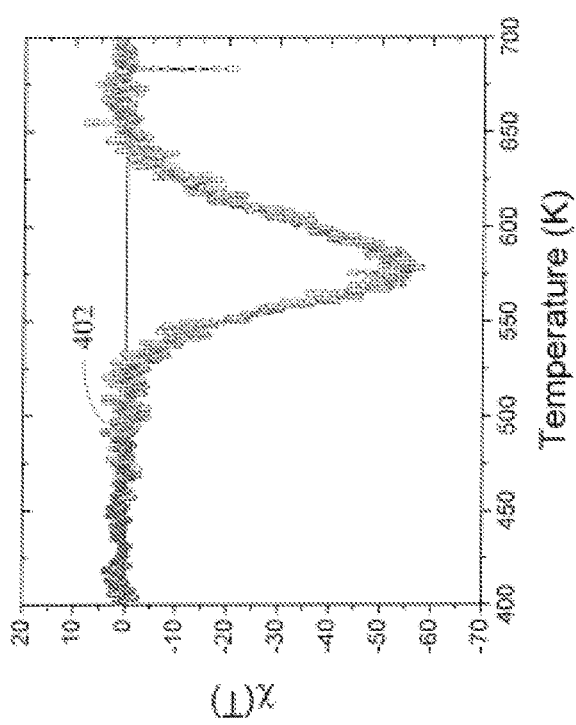
FIG. 4 shows the temperature dependency of imaginary AC susceptibility, $\chi(T)$, for a representative sample of HAMR material in accordance with various embodiments.

Determining Tc distribution in accordance with embodiments of the disclosure involves measuring the imaginary part of AC susceptibility of the magnetic material sample as a function of temperature, described by the function $\chi_i(T)$. During testing, the sample is heated using a heating stage within a temperature ranging from room temperature up to at least about 600° C., for example, with the assumption that the mean Curie temperature for the sample is some temperature between ambient and 600° C. As is indicated in FIG. 4, it may be productive to heat the sample to a temperature well above the Curie temperature, such as 700° C., for example. Using a MOKE detection scheme, such as those discussed hereinbelow, the imaginary part of AC susceptibility is measured while the sample is subjected to an AC field and heating within a temperature range that includes the mean Curie temperature of the sample.

FIG. 4 shows the temperature dependency of imaginary AC susceptibility, $\chi_i(T)$, for a representative sample of HAMR material. It can be seen in FIG. 4 that the $\chi_i(T)$ curve 402 has a peak and a width. Theoretical calculations and simulations show that the peak position of the $\chi_i(T)$ curve 402 contains the mean Tc, and that the width of the $\chi_i(T)$ curve 402 contains information on Tc distribution. It has been determined by the inventors that the width of the $\chi_i(T)$ curve 402 is related (e.g., proportional) to the standard deviation of the Tc distribution. For example, the width of the $\chi_i(T)$ curve 402 is greater for wider Tc distribution (larger standard deviation of the Tc distribution ($\delta(Tc)$). Conversely, the width of the $\chi_i(T)$ curve 402 is smaller for tighter Tc distribution (small standard deviation of the Tc distribution ($\delta(Tc)$)).

Figure 5A:
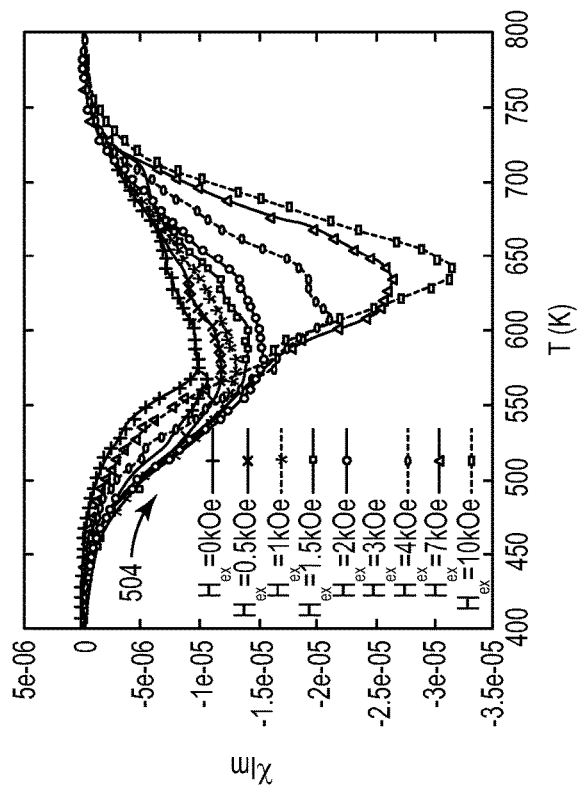
FIGS. 5A and 5B show representative kinetic Monte-Carlo modeling results of sensitivity of an $\chi(T)$ curve on different Tc distributions and different exchange couplings (Hex) in accordance with various embodiments.
Figure 5B:
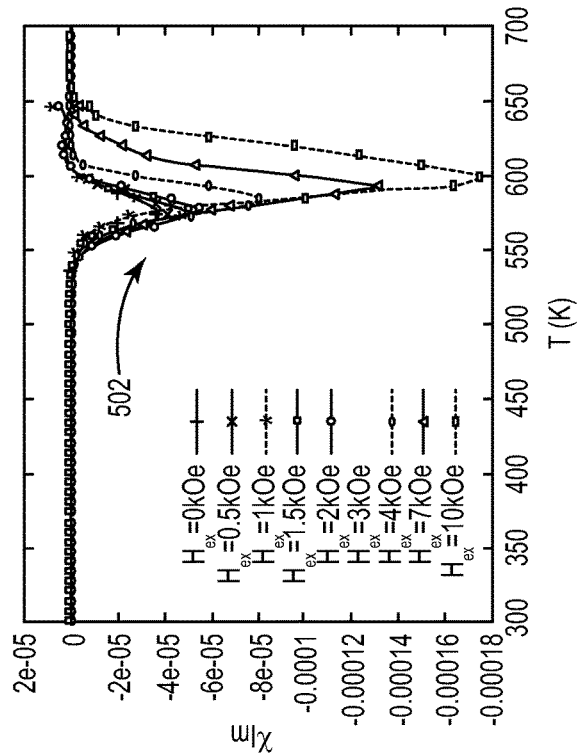

FIGS. 5A and 5B show representative kinetic Monte-Carlo modeling results of sensitivity of an $\chi_i(T)$ curve on different Tc distributions and different exchange couplings (Hex) in accordance with various embodiments. FIG. 5A corresponds to modeling results 502 of an $\chi_i(T)$ curve for $\delta(Tc)=0$. FIG. 5B corresponds to modeling results 504 of an $\chi_i(T)$ curve for $\delta(Tc)=10\%$. FIGS. 5A and 5B demonstrate that larger Tc distributions (e.g., 10%) show much wider peaks in the $\chi_i(T)$ curve and contain information for $\delta(Tc)$. FIGS. 5A and 5B further show that intergranular exchange coupling (Hex) has an impact on the width of $\chi_i(T)$. In order to extract $\delta(Tc)$, Hex can be used as one of the input parameters, which may be determined using various known techniques such as from recoil loop measurements. Fortuitously, the intergranular exchange coupling for most HAMR media of interest is small due to the presence of a significant amount of non-magnetic material (e.g., carbon, oxide) in the grain boundary used to decouple the grains. Hence it has weak effects on the accuracy of the methods. Nevertheless, intergranular exchange coupling can be quantified, such as by measuring recoil loops and extracting the interaction field, and used for extracting Tc distribution in accordance with embodiments of the disclosure.

Figure 6:
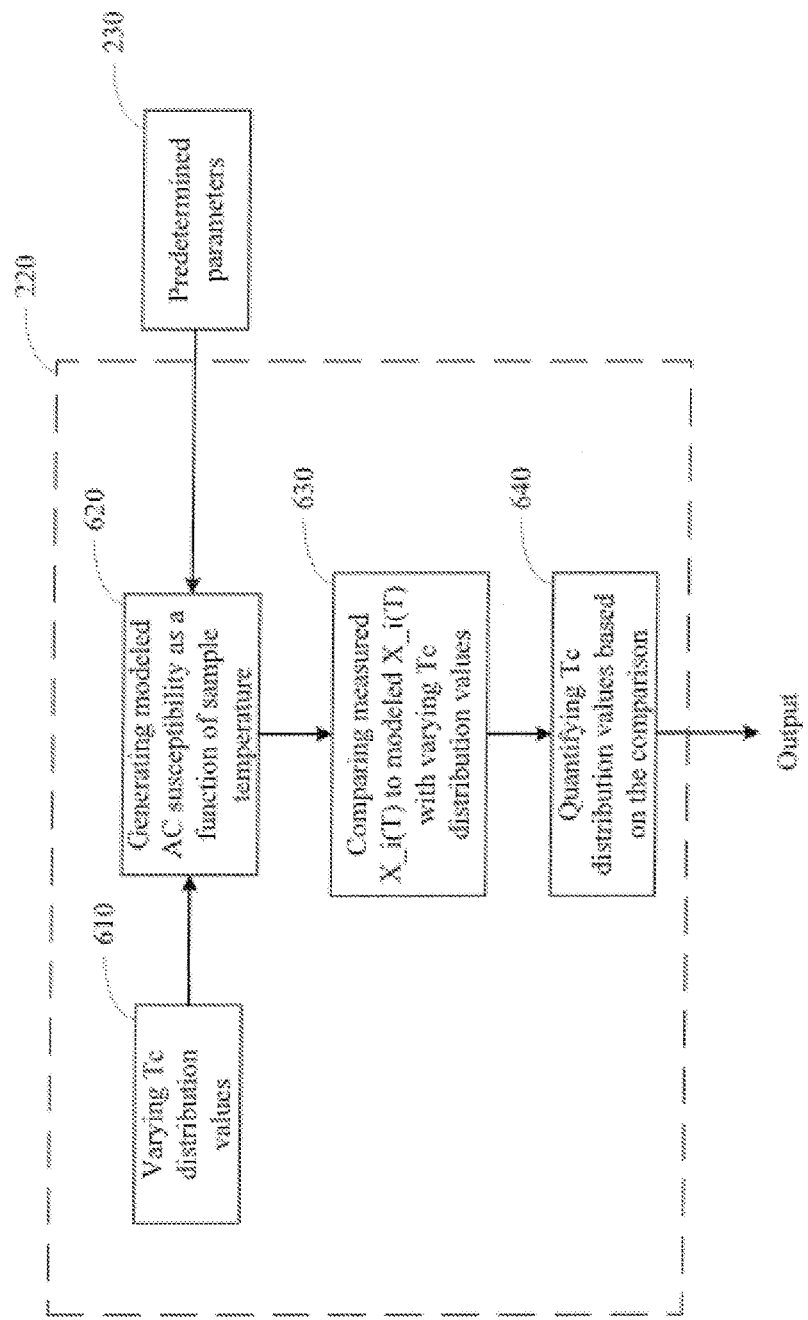
FIG. 6 illustrates various processes for determining a Tc distribution for a magnetic material sample in accordance with various embodiments.

FIG. 6 illustrates various processes for determining 220 a Tc distribution for a magnetic material sample in accordance with various embodiments. The methodology illustrated in FIG. 6 involves generating 620 modeled imaginary AC susceptibility $\chi_i(T)$ as a function of the temperature of the magnetic material sample. With a number of predetermined parameters 230 associated with the magnetic material, a multiplicity of modeled $\chi_i(T)$ curves are generated for varying Tc distribution values 610. The methodology further involves comparing 630 the measured $\chi_i(T)$ to the modeled $\chi_i(T)$ with respect for varying Tc distribution values 610. Based on this comparison, Tc distribution values of the magnetic material sample are quantified 640. These values (e.g., signals or data representing these values) may be output in various forms as previously discussed.

Figure 7:
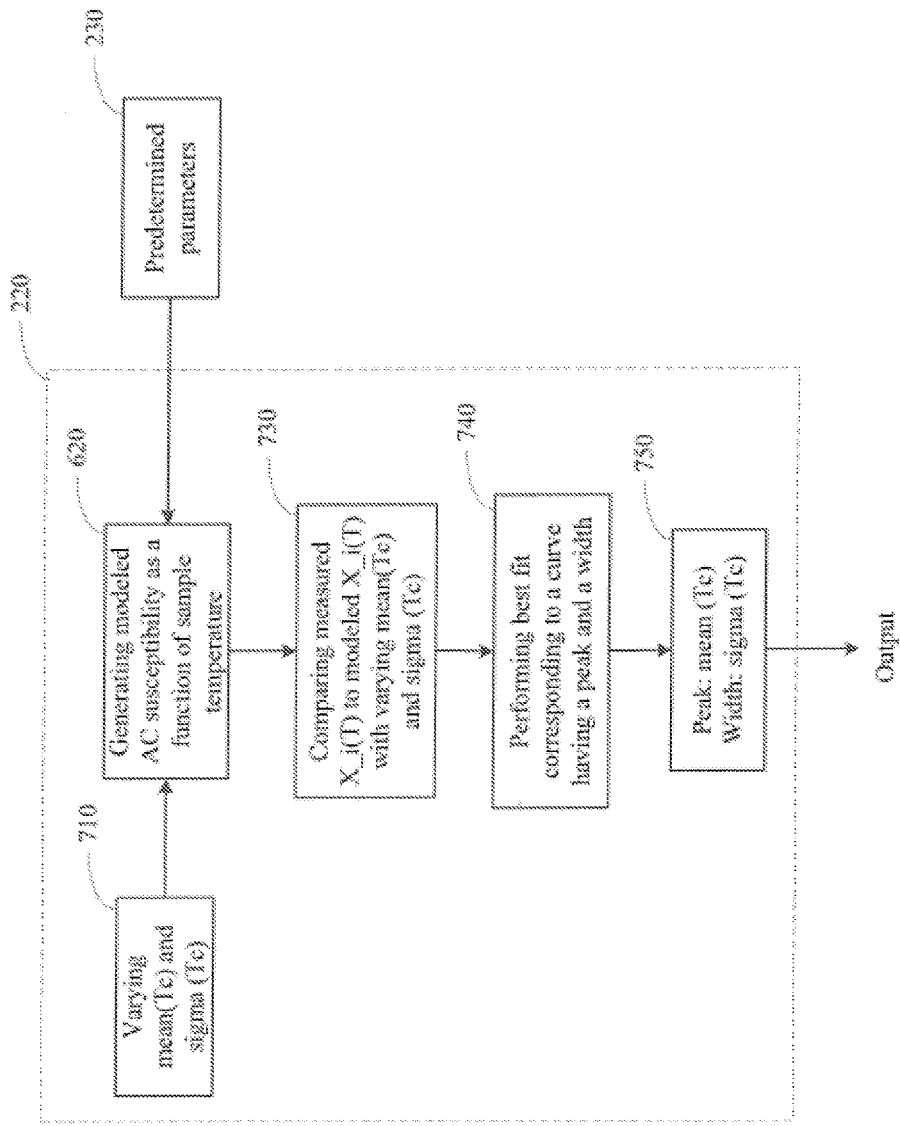
FIG. 7 illustrate various processes for determining a Tc distribution for a magnetic material sample including performing a best fit curve process between the measured $\chi(T)$ curve and the modeled $\chi(T)$ curves in accordance with various embodiments.

According to some embodiments consistent with the methodology shown in FIG. 6, the Tc distribution values include the mean of the Tc distribution (mean(Tc)) and the standard deviation of the Tc distribution ($\delta(Tc)$), and the corresponding processes of comparing and quantifying are illustrated in FIG. 7. After generating 620 the modeled $\chi_i(T)$ curves with predetermined parameters 230 and varying mean(Tc) and $\delta(Tc)$ 710, FIG. 7 shows the process of comparing 730 the measured $\chi_i(T)$ to the modeled $\chi_i(T)$. This comparison 730 is made with respect to varying mean(Tc) and $\delta(Tc)$ values. Preferably, the range and step of these modeled mean(Tc) and $\delta(Tc)$ values are determined based on some educated estimate of the real mean(Tc) and $\delta(Tc)$ for a given magnetic material sample. Preferably, the Tc distribution of the given magnetic material sample follows a lognormal distribution which is characterized by its mean(Tc) and $\delta(Tc)$.

FIG. 7 further shows performing 740 a best fit curve process between the measured $\chi_i(T)$ curve and the modeled $\chi_i(T)$ curves. The modeled $\chi_i(T)$ curve that best matches the measured $\chi_i(T)$ curve is identified as the best fit curve, which includes a peak and a width. Based on the position of the peak of the best fit curve, a mean of the Tc distribution is quantified 750. Based on the width information of the best fit curve, a standard deviation of the Tc distribution is quantified 750.

As discussed previously, other parameters such as distributions of anisotropy and grain volume ($\delta(H_k)$ and $\delta(V)$), intergranular exchange coupling (Hex), and thermal stability factor ($K_U V/k_B T$) also affect the AC susceptibility and hence the imaginary AC susceptibility $\chi_i(T)$ curve. These quantities can be measured and determined individually using various known methods such as field dependence of susceptibility and dynamical coercivity. Using a specified number of these predetermined parameters along with analytical formulae and theoretical modeling, Tc distribution can be extracted by identifying the best fit measured $\chi_i(T)$ curve.

Figure 8:
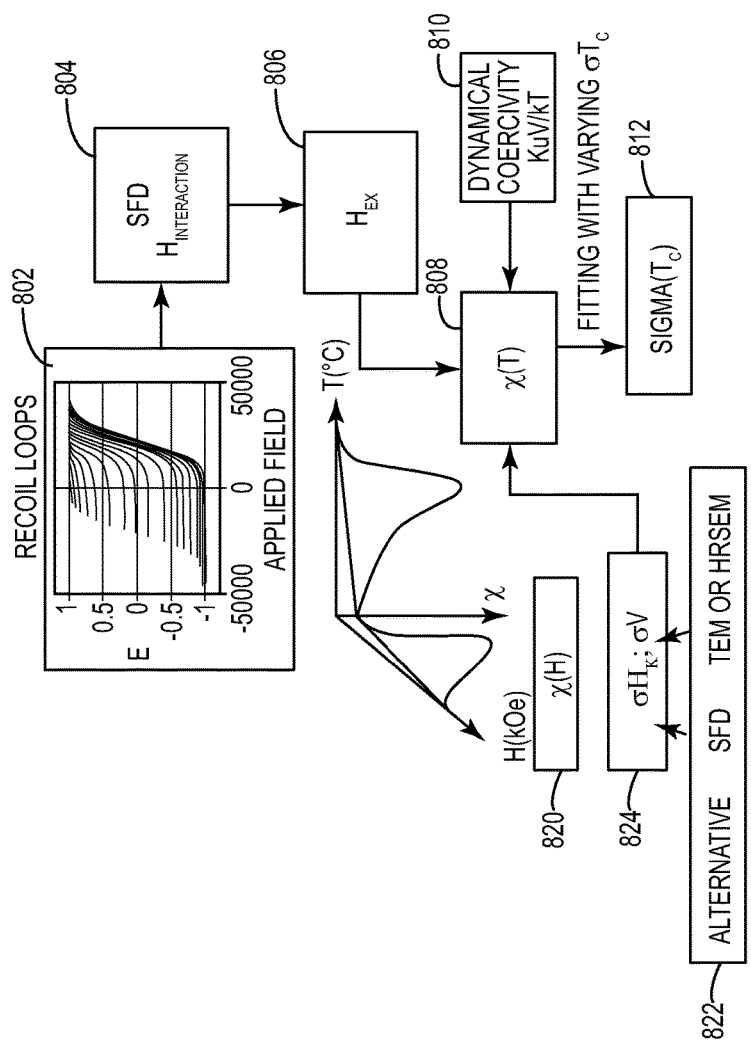
FIG. 8 is a flow chart of various parameters that can be used in addition to temperature dependent AC susceptibility data for determining Tc distribution in accordance with various embodiments.

FIG. 8 is a flow chart of other parameters that can be used in addition to temperature dependent AC susceptibility data for determining Tc distribution. For example, intergranular exchange coupling, Hex 806, can be measured using recoil loop measurements 802 and a switching field distribution (SFD) 804 over the temperature range of interest. Saturation magnetization (Ms) and thermal stability factor ($K_U V/k_B T$) can be determined from dynamical coercivity measurements 810. Anisotropy ($H_k$) 820 can be determined from VSM measurement. Distributions of anisotropy and grain volume ($\delta(H_k)$ and $\delta(V)$) can be determined from temperature dependent transverse AC susceptibility measurements, as described in previously incorporated U.S. Pat. No. 7,166,997. An alternative method 822 of determining $\delta(H_k)$ and $\delta(V)$ is to estimate $\delta(H_k)$ from a switching field distribution, SFD, and obtain $\delta(V)$ from SEM or TEM images. A typical $\delta(H_k)$ is about 5% less than SFD in absolute percentage values, and the temperature dependence of the susceptibility $\chi_i(T)$ curve is not very sensitive to $\delta(H_k)$.

Some or all of these measured parameters are combined as an input to a kinetic Monte-Carlo model with varying $\delta(Tc)$ to generate multiple modeled $\chi_i(T)$ curves 808. After measuring the temperature dependent AC susceptibility $\chi_i(T)$ of the magnetic material sample, a comparison is performed between the experimental $\chi_i(T)$ data and modeling results with different $\delta(Tc)$, and the best fit curve gives rise to $\delta(Tc)$ 812. While $\delta(Tc)$ is of greater interest in assessing and enhancing HAMR media, the processes described herein can be used to determine the mean(Tc). According to one approach, matching the peak position of the experimental $\chi_i(T)$ curve by modeled $\chi_i(T)$ curves with varying mean(Tc) can give rise to mean(Tc), taking into consideration of the measured thermal stability factor. According to other approaches, mean(Tc) can be extracted by measuring magnetization as a function of temperature.

Although many parameters other than Tc distribution can affect $\chi_i(T)$, some or all of these parameters may only weakly influence $\chi_i(T)$. The sensitivity of $\chi_i(T)$ to parameters other than Tc distribution depends in large part on the value of such other parameters. For example, intergranular exchange (Hex) may weakly impact $\chi_i(T)$ if Hex is weak. Conversely, Hex can have a significant impact on $\chi_i(T)$ if Hex is strong. Accordingly, it is important to obtain at least a rough estimate of the range of Hex, even though the absolute value of Hex is not as important. By way of non-limiting example, Hex generally has an impact on $\chi_i(T)$, but the impact on the shape of the $\chi_i(T)$ curve is minimal (negligible) when the Hex/$H_k$ ratio is below 0.05. A similar approach to evaluating the impact on $\chi_i(T)$ by parameters other than Tc distribution can be taken for sigma(Hk), for example. When KuV/kT is high, $\chi_i(T)$ is less sensitive to sigma(Hk). However, when KuV/kT is low, $\chi_i(T)$ becomes more sensitive to sigma(Hk). As in the case of Hex discussed above, it is important to obtain at least a rough estimate of sigma(Hk) for the range of typical HAMR media due to its high thermal stability.

Figure 9:
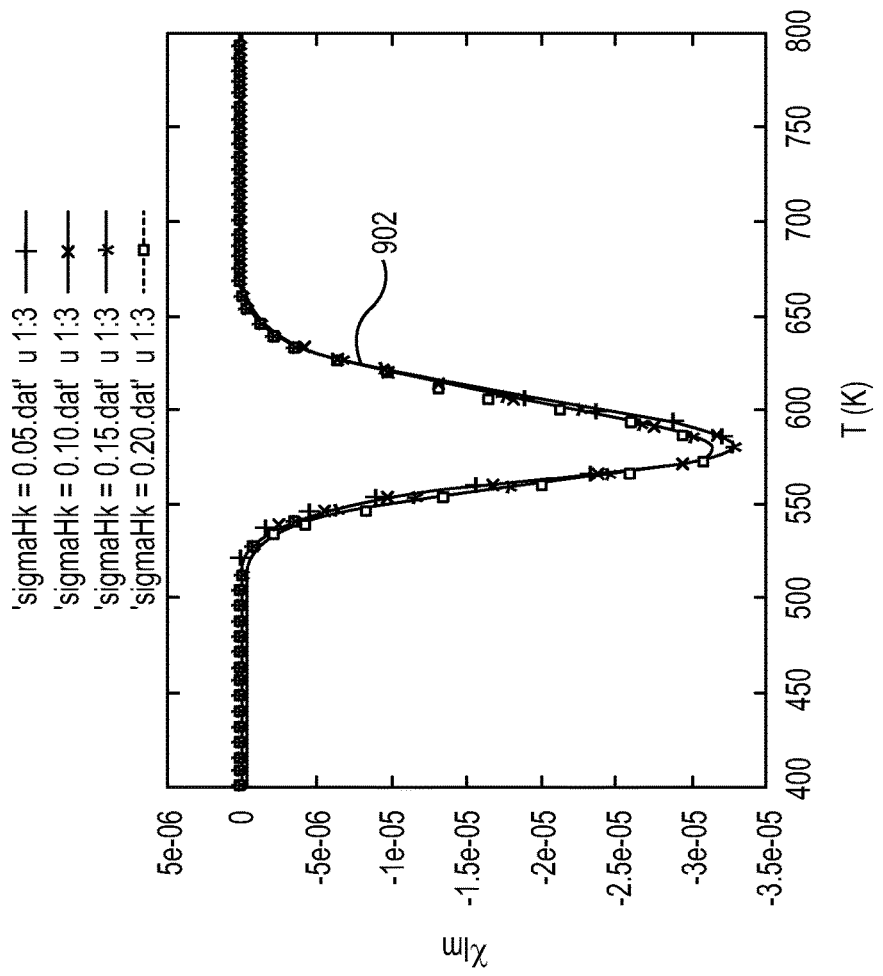
FIG. 9 illustrates the relative insensitivity of $\chi(T)$ to anisotropy distribution of a magnetic material typical used in HAMR media in accordance with various embodiments.

Since for most relevant HAMR media, the grains are well isolated and decoupled for both magnetic and thermal design requirements, Hex is rather small (0-2 kOe), hence it has a weak effect on the accuracy of the methods described herein. Another example is $\delta(H_k)$. As can be seen in FIG. 9, $\chi_i(T)$ (shown as curve 902) is relatively insensitive to $\delta(H_k)$ (ranging from 5 to 20%) for various typical HAMR media parameters (high $H_k$~50-80 kOe; high $K_U V/k_B T$~150-300). This insensitivity to $\delta(H_k)$ is due to the peak position of $\chi_i(T)$ curve when the temperature of the magnetic material sample falls within a temperature range close to Tc, with large $H_k$ and $K_U V/k_B T$ for HAMR media. Hence, $\chi_i(T)$ has greater sensitivity to $\delta(Tc)$ than to $\delta(H_k)$. This is similar to the relationship between switching field and $\delta(Tc)$ and the relationship between switching field and $\delta(H_k)$, illustrated in FIGS. 1A and 1B.

Figure 10:
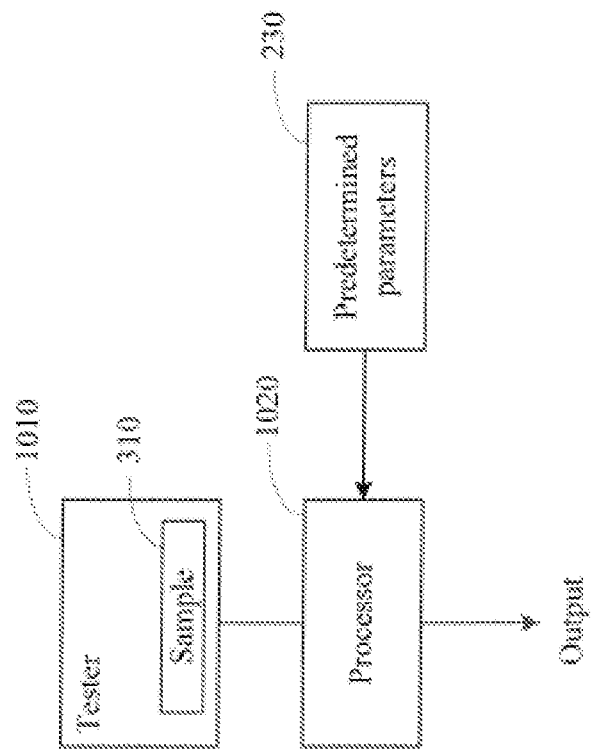
FIGS. 10-12 show apparatuses for determining a Tc distribution of a magnetic material sample in accordance with various embodiments.

FIG. 10 shows an apparatus for determining a Tc distribution of a magnetic material sample 310 in accordance with various embodiments. The apparatus shown in FIG. 10 includes a tester 1010 configured to produce temperature dependent AC susceptibility data for the magnetic material sample 310. The apparatus further includes a processor configured to determine a Tc distribution of the sample based on the tester data and a multiplicity of predetermined parameters 230 of the sample. Various forms of output based on the Tc distribution can be reproduced.

Figure 11:
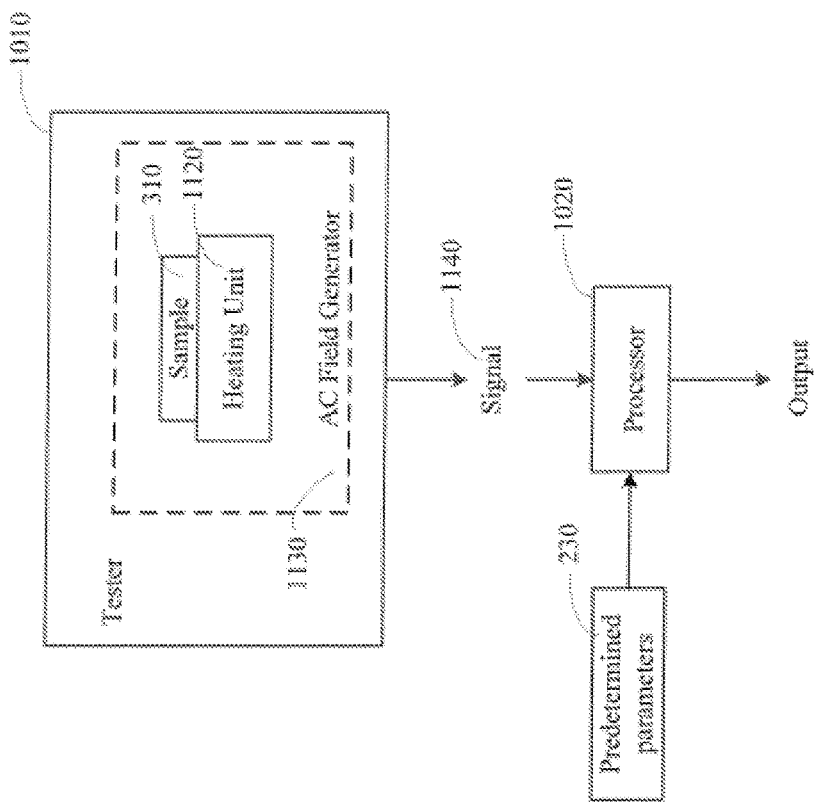

FIG. 11 shows an embodiment of an apparatus for determining Tc distribution for a sample 310 comprising magnetic material in accordance with various embodiments. The embodiment shown in FIG. 11 includes an electromagnetic field generator 1130, preferably an AC field generator, that generates an AC field to which the magnetic sample 310 is subjected. The AC field produced by the AC field generator 1130 may have a frequency of 500 Hz, for example. The apparatus shown in FIG. 12 further includes a heating unit 1120 operable for heating the sample 310 over a range of temperatures, which preferably includes a range of temperatures below and above a known mean of the Curie temperature of the magnetic material sample 310.

The tester 1010 is configured to generate a signal 1140 representative of a parameter of the sample 310 that changes as a function of changing sample temperature while the sample 310 is subjected to the electromagnetic field produced by the AC field generator 1130. Preferably, the signal 1140 is representative of a magnetic state of the sample 310. More preferably, the signal 1140 is representative of a temperature dependent AC susceptibility of the sample 310. The apparatus of FIG. 11 further includes a processor 1020 having an input for receiving the signal 1140 generated by the tester 1010. The processor 1020 is configured to determine Tc distribution of the sample 310 using the generated signal 1140 and a multiplicity of predetermined parameters 230 of the sample 310. The processor 1020 preferably includes a microprocessor coupled to memory. The memory is configured to store program code and algorithms which, when executed by the microprocessor, cause the microprocessor to perform various processes for determining Tc distribution of the sample 310 in accordance with the various embodiments described herein.

Figure 12:
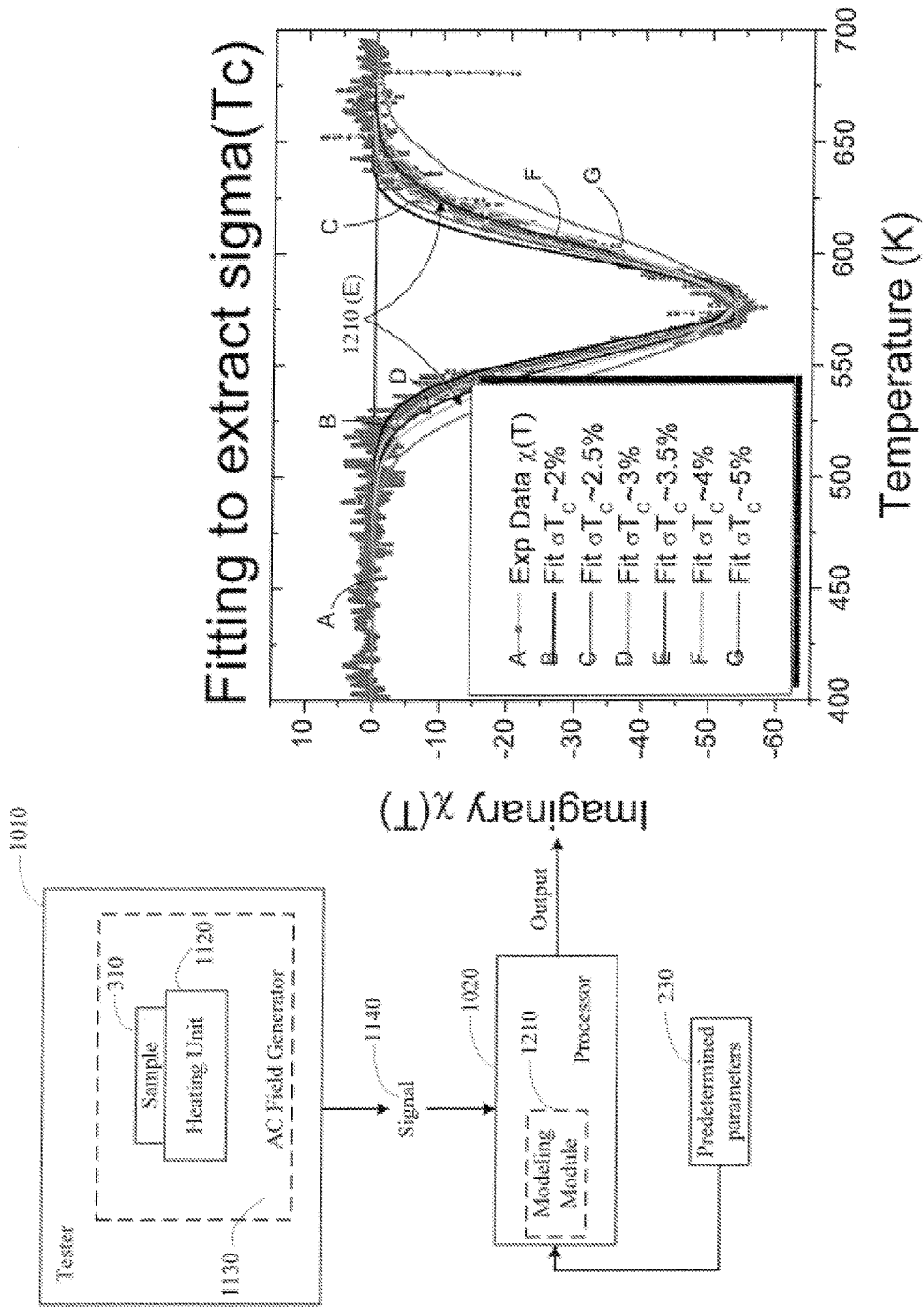

FIG. 12 shows an embodiment of an apparatus for determining Tc distribution for a sample 310 comprising magnetic material in accordance with various embodiments. In addition to the components shown in the embodiment of FIG. 11, the apparatus illustrated in FIG. 12 includes a modeling module 1210 configured to generate modeling results of imaginary AC susceptibility $\chi_i(T)$ as a function of temperature of the sample 310 using a specified number of predetermined parameters and varying Tc distribution values as discussed previously. Preferably, the varying Tc distribution values include mean(Tc) and $\delta$(Tc). The processor 1020 is configured to compare data corresponding to a component of the signal 1140 produced by the tester 1010 with a corresponding component of the modeled AC susceptibility data with varying Tc distribution values, and quantify Tc distribution values based on the comparison.

The processor 1020 is configured to compare the imaginary AC susceptibility $\chi_i(T)$ with modeled AC susceptibility $\chi_i(T)$ with varying mean(Tc) and $\delta$(Tc). The processor 1020 is also configured to perform a best fit of the data corresponding to a component of the signal 1140 with the modeled AC susceptibility data, wherein the best fit corresponds to a curve 1210 having a peak and a width. The peak corresponds to a mean of the Tc distribution and the width corresponds to a standard deviation of the Tc distribution.

Preferably, the component is the imaginary part of AC susceptibility $\chi_i(T)$, and the best fit is among multiple modeled $\chi_i(T)$ curves with varying mean(Tc) and $\delta$(Tc).

FIG. 12 illustrates one example of an output of the processor 1020 in accordance with one embodiment. In the representative example shown in FIG. 12, multiple $\chi_i(T)$ curves (labeled B-G) are modeled with varying $\delta$(Tc) from 2% to 5%, with other media parameters (e.g., $H_k$ and distribution, Tc, grain size and distribution; and exchange Hex~2 kOe) set to predetermined values. Tc distribution is extracted by fitting the experimental data (curve A) from the signal 1140 with multiple modeled $\chi_i(T)$ curves (B-G). The best fit results show that $\delta$(Tc) is around 3.5% for this particular sample of magnetic material, indicated by curve E. It is noted that a sensitivity of less than 0.5% can be achieved, and that this sensitivity can be determined by the measured $\chi_i(T)$ signal 1140 quality. In context of various embodiments, data quality can be expressed as a signal-to-noise ratio (SNR) of the data, which usually needs to be better than 10. Alternative, the fitting sensitivity can be gauged by the mean square error of the fit, which can help to determine the accuracy of the method within about 0.5%. Mean(Tc) in this particular example is determined by the peak of the best fit curve, curve E.

Figure 13:
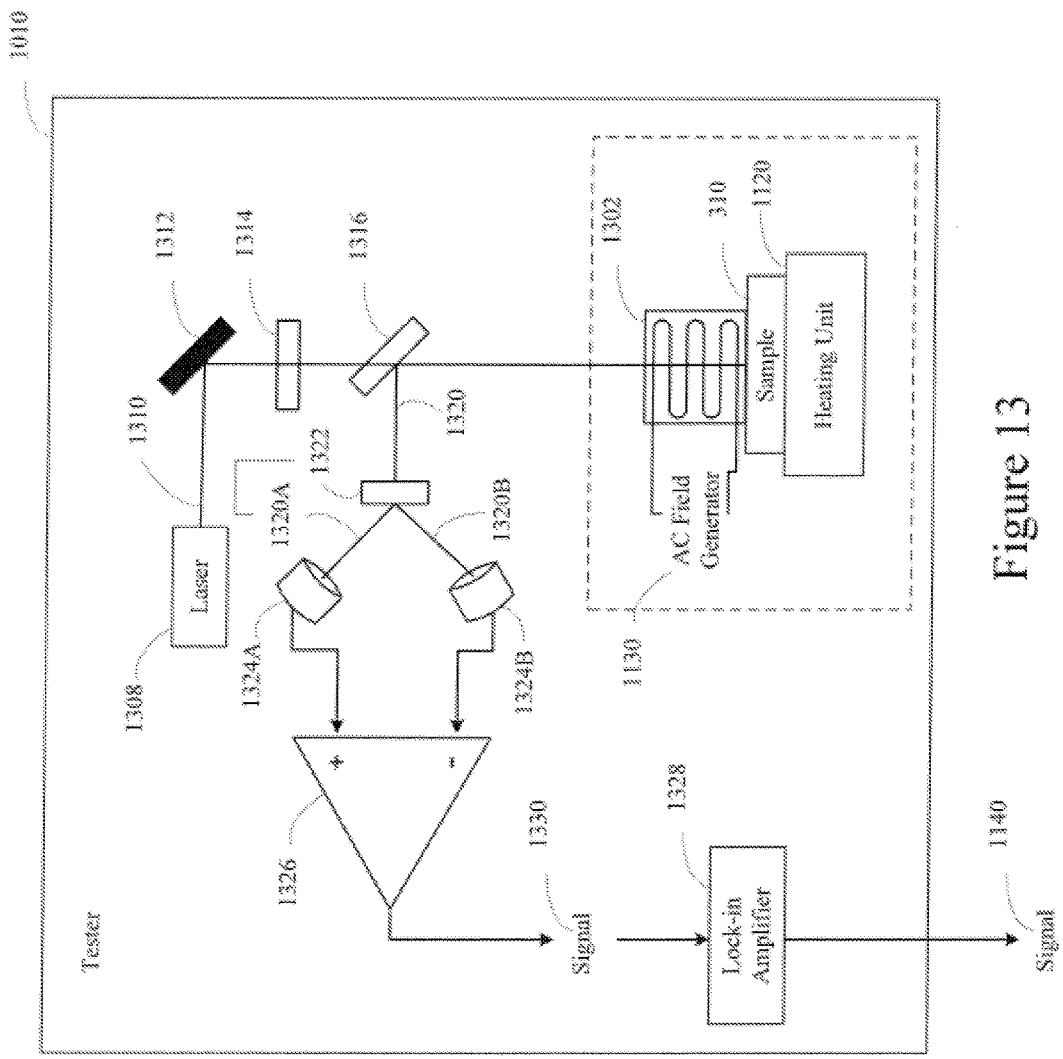
FIG. 13 is a schematic layout of a tester apparatus for determining a Tc distribution of a magnetic sample in accordance with various embodiments.

FIG. 13 is a schematic layout of a tester 1010 included in an apparatus for determining the Tc distribution of a magnetic sample 310 in accordance with various embodiments. In this embodiment, the tester 1010 includes a Magneto-Optical Kerr Effect (MOKE) detector, which includes AC coil 1302, AC field generator 1130, heating unit 1120, He-Ne laser 1308 (which produces incident beam 1310), mirror 1312, polarizer 1314, beam splitter 1316, Wollostan prism (or analyzer) 1322, photodiodes 1324A and 1324B, differential amplifier 1326, and lock-in amplifier 1328. In FIG. 13, a magnetic sample 310 is positioned on a heating unit 1120 which provides heating of the sample 310 from room temperature to a temperature (e.g., 600-700° C.) above the estimated mean Curie temperature of sample 310, and also provides optical access to the sample surface. Mechanical stability and an inert environment with a $N_2$ purging capability are important to the performance of the apparatus shown in FIG. 13.

During MOKE testing, the magnetic sample 310 is subjected to an AC field which is oriented perpendicular to the plane of the sample 310. The AC field (typically several tens of Oe) is generated using AC coil 1302 and AC field generator 1130. A laser 1308, such as a He—Ne laser, serves as a light source for the MOKE probe. Incident beam 1310 produced by the laser 1308 is reflected by mirror 1312, and passes through polarizer 1314 and beam splitter 1316. Incident beam 1310 is reflected at the surface of sample 310 and undergoes a polarization alteration due to the magnetization of sample 310. Reflected beam 1320 is reflected by beam splitter 1316 to a detection arm which includes Wollaston prism 1322 and photodiodes 1324A and 1324B.

Wollaston prism 1322, or other analyzer, is used to separate polarized beam components 1320A and 1320B of the reflected beam 1320. Photodiodes 1324A and 1324B provide positive and negative input signals to differential amplifier 1326. The output of differential amplifier 1326 is a signal 1330 representing a difference in intensity of components 1320A and 1320B of the reflected beam 1320, which is proportional to the change of magnetization induced by the AC field. Lock-in amplifier 1328, using the output signal 1330 from differential amplifier 1326, is configured to determine the real and imaginary components of the signal 1330 and generate an output signal 1140.

It is to be understood that even though numerous characteristics and advantages of various embodiments disclosed herein have been set forth in the foregoing description, together with details of the structure and function of various embodiments, this detailed description is illustrative only, and changes may be made in detail, especially in matters of structure and arrangements of parts within the principles of the presently disclosed subject matter to the full extent indicated by the broad general meaning of the terms in which the appended claims are expressed.

What is claimed is:
1. A method, comprising:
subjecting a sample comprising magnetic material to an AC electromagnetic field;
heating the sample over a range of temperatures;
generating, by a tester apparatus, a signal representative of an imaginary part of AC susceptibility of the sample that changes as a function of changing sample temperature while the sample is subjected to the AC electromagnetic field; and
determining, by a processor, a Curie temperature (Tc) distribution of the sample using the generated signal and a plurality of predetermined parameters of the sample.

2. The method of claim 1, wherein the signal is representative of a magnetic state of the sample, the magnetic state of the sample changing as a function of changing sample temperature.

3. The method of claim 1, wherein:
determining the Tc distribution comprises analyzing changes of a component of the signal over the range of temperatures.

4. The method of claim 3, wherein the component comprises an imaginary component of the signal.

5. The method of claim 1, wherein:
the predetermined parameters comprise at least a thermal stability factor and a grain volume distribution.

6. The method of claim 1, wherein:
the predetermined parameters comprise at least a thermal stability factor, a grain volume distribution, and an intergranular exchange coupling parameter.

7. The method of claim 1, wherein the temperature range comprises a range of temperatures above and below a known mean Curie temperature for the magnetic material of the sample.

8. The method of claim 1, wherein determining the Tc distribution comprises:
generating modeled AC susceptibility data as a function of sample temperature change using the predetermined parameters and varying Tc distribution values.

9. The method of claim 8, wherein the varying Tc distribution values comprises a standard deviation of the Tc distribution.

10. The method of claim 1, wherein determining the Tc distribution comprises:
generating modeled AC susceptibility data as a function of sample temperature change using the predetermined parameters and varying Tc distribution values;
comparing data corresponding to a component of the signal with a corresponding component of the modeled AC susceptibility data with varying Tc distribution values; and
quantifying Tc distribution values based on the comparison.

11. The method of claim 10, comprising performing a best fit of the data corresponding to a component of the signal with the modeled AC susceptibility data.

12. The method of claim 11, wherein:
the best fit corresponds to a curve having a peak and a width;
the peak corresponds to a mean of the Tc distribution; and
the width corresponds to a standard deviation of the Tc distribution.

13. The method of claim 1, further comprising producing a data signal representative of the Tc distribution.

14. A method comprising:
acquiring, by a tester apparatus, temperature dependent AC susceptibility data for a sample comprising magnetic material, the AC susceptibility data comprising an imaginary part of AC susceptibility for the sample; and
determining, by a processor, a Curie temperature (Tc) distribution of the sample based on the acquired data and a plurality of predetermined parameters of the sample.

15. The method of claim 14, wherein the AC susceptibility data comprises the imaginary part of AC susceptibility for the sample as a function of sample temperature.

16. The method of claim 14, wherein determining the Tc distribution comprises analyzing changes of the AC susceptibility data over a range of temperatures.

17. The method of claim 14, wherein the predetermined parameters comprise at least a thermal stability factor and a grain volume distribution.

18. The method of claim 14, wherein the predetermined parameters comprise at least a thermal stability factor, a grain volume distribution, and an intergranular exchange coupling parameter.

19. The method of claim 14, comprising generating modeled AC susceptibility data as a function of sample temperature change using the predetermined parameters and varying Tc distribution values, the varying Tc distribution values comprising a standard deviation of the Tc distribution.

20. The method of claim 1, wherein:
the data defines a curve having a peak and a width;
the peak is representative of a mean of the Tc distribution; and
the width is representative of the Tc distribution.

* * * * *